US008212096B2

(12) United States Patent
Roth et al.

(10) Patent No.: US 8,212,096 B2
(45) Date of Patent: Jul. 3, 2012

(54) HYDROALKYLATION OF AROMATIC COMPOUNDS USING EMM-13

(75) Inventors: Wieslaw J. Roth, Sewell, NJ (US);
Terry E. Helton, Bethlehem, PA (US);
Jane C. Cheng, Bridgewater, NJ (US);
Michael J. Brennan, Scotch Plains, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 12/994,278

(22) PCT Filed: Jul. 15, 2009

(86) PCT No.: PCT/US2009/050717
§ 371 (c)(1),
(2), (4) Date: Nov. 23, 2010

(87) PCT Pub. No.: WO2010/014401
PCT Pub. Date: Feb. 4, 2010

(65) Prior Publication Data
US 2011/0077438 A1    Mar. 31, 2011

Related U.S. Application Data

(60) Provisional application No. 61/084,171, filed on Jul. 28, 2008.

(51) Int. Cl.
*C07C 2/66* (2006.01)
(52) U.S. Cl. ...................................................... 585/467
(58) Field of Classification Search .................. 585/467
See application file for complete search history.

(56) References Cited

U.S. PATENT DOCUMENTS

| | | | |
|---|---|---|---|
| 3,197,399 A | 7/1965 | Wight et al. |
| 3,201,356 A | 8/1965 | Kress et al. |
| 3,347,945 A | 10/1967 | Slaugh |
| 3,390,101 A | 6/1968 | Csicsery |
| 3,412,165 A | 11/1968 | Slaugh et al. |
| 3,536,771 A | 10/1970 | Graff |
| 3,751,504 A | 8/1973 | Keown et al. |
| 3,760,017 A | 9/1973 | Arkell et al. |
| 3,760,018 A | 9/1973 | Suggitt et al. |
| 3,760,019 A | 9/1973 | Crone, Jr. et al. |
| 3,784,617 A | 1/1974 | Suggitt et al. |
| 3,784,618 A | 1/1974 | Suggitt et al. |
| 3,839,477 A | 10/1974 | Suggitt et al. |
| 3,864,421 A | 2/1975 | Suggitt |
| 3,957,687 A | 5/1976 | Arkell et al. |
| 3,962,362 A | 6/1976 | Suggitt |
| 4,016,218 A | 4/1977 | Haag et al. |
| 4,021,490 A | 5/1977 | Hudson |
| 4,094,918 A | 6/1978 | Murtha et al. |
| 4,122,125 A | 10/1978 | Murtha et al. |
| 4,152,362 A | 5/1979 | Murtha |
| 4,177,165 A | 12/1979 | Murtha et al. |
| 4,206,082 A | 6/1980 | Murtha et al. |
| 4,219,687 A | 8/1980 | Dolhyj et al. |
| 4,219,689 A | 8/1980 | Murtha |
| 4,268,699 A | 5/1981 | Murtha et al. |
| 4,329,531 A | 5/1982 | Murtha et al. |
| 4,380,683 A | 4/1983 | Dolhyj et al. |
| 4,439,409 A | 3/1984 | Puppe et al. |
| 4,447,554 A | 5/1984 | Murtha et al. |
| 4,547,605 A | 10/1985 | Kresge et al. |
| 4,826,667 A | 5/1989 | Zones et al. |
| 4,891,458 A | 1/1990 | Innes et al. |
| 4,954,325 A | 9/1990 | Rubin et al. |
| 4,954,663 A | 9/1990 | Marler et al. |
| 4,956,514 A | 9/1990 | Chu |
| 4,962,239 A | 10/1990 | Bell et al. |
| 4,962,250 A | 10/1990 | Dessau et al. |
| 4,962,255 A | 10/1990 | Fraenkel et al. |
| 4,962,256 A | 10/1990 | Le et al. |
| 4,962,257 A | 10/1990 | Absil et al. |
| 4,968,402 A | 11/1990 | Kirker et al. |
| 4,973,784 A | 11/1990 | Han et al. |
| 4,982,033 A | 1/1991 | Chu et al. |
| 4,982,040 A | 1/1991 | Angevine et al. |
| 4,983,276 A | 1/1991 | Absil et al. |
| 4,986,894 A | 1/1991 | Keville et al. |
| 4,992,606 A | 2/1991 | Kushnerick et al. |
| 4,992,611 A | 2/1991 | Morrison |
| 4,992,615 A | 2/1991 | Huss, Jr. et al. |
| 5,000,839 A | 3/1991 | Kirker et al. |
| 5,001,283 A | 3/1991 | Altman et al. |

(Continued)

FOREIGN PATENT DOCUMENTS

EP    0 293 032    11/1988

(Continued)

OTHER PUBLICATIONS

I. Borodina et al., "Hydroalkylation of Benzene and Ethylbenzene over Metal Containing Zeolite Catalysts", Microporous and Mesoporous Materials, 2007, vol. 105, pp. 181-188.
W. Fan et al., "Synthesis and Catalytic Properties of a New Titanosilicate Molecular Sieve with the Structure Analogous to MWW-type Lamellar Precursor", Journal of Catalyst, 2006, vol. 243, pp. 183-191.
S. Kim et al., "Structural Evolution of B-MCM-36 and B-ITQ-2 from B-MCM-22", Bull. Korean Chem. Society, 2006, vol. 27, No. 10, pp. 1693-1696.
S. Lawton et al., "Zeolite MCM-49: A Three-Dimensional MCM-22 Analogue Synthesized by in Situ Crystallization", Journal of Physical Chemistry, 1996, vol. 100, pp. 3788-3798.
S. Maheshwari et al., "Layer Structure Preservation During Swelling, Pillaring, and Exfoliation of a Zeolite Precursor", Journal of American Chemical Soc., 2008, vol. 130, pp. 1507-1516.

(Continued)

Primary Examiner — Thuan Dinh Dang
(74) Attorney, Agent, or Firm — Jamie L. Sullivan

(57) ABSTRACT

This disclosure relates to a process for manufacturing a mono-cycloalkyl-substituted aromatic compound, said process comprising contacting a feedstock comprising an aromatic compound and hydrogen under hydroalkylation reaction conditions with a catalyst system comprising a molecular sieve, wherein said molecular sieve comprises a framework of tetrahedral atoms bridged by oxygen atoms, the tetrahedral atom framework being defined by a unit cell with atomic coordinates in nanometers shown in Table 2.

23 Claims, 1 Drawing Sheet

U.S. PATENT DOCUMENTS

| | | | |
|---|---|---|---|
| 5,001,295 | A | 3/1991 | Angevine et al. |
| 5,001,296 | A | 3/1991 | Howley et al. |
| 5,012,033 | A | 4/1991 | Child et al. |
| 5,013,422 | A | 5/1991 | Absil et al. |
| 5,019,664 | A | 5/1991 | Del Rossi et al. |
| 5,019,665 | A | 5/1991 | Partridge et al. |
| 5,019,670 | A | 5/1991 | Le et al. |
| 5,037,538 | A | 8/1991 | Chin et al. |
| 5,053,571 | A | 10/1991 | Makkee |
| 5,108,969 | A | 4/1992 | Del Rossi et al. |
| 5,146,024 | A | 9/1992 | Reed |
| 5,236,575 | A | 8/1993 | Bennett et al. |
| 5,250,277 | A | 10/1993 | Kresge et al. |
| 5,292,976 | A | 3/1994 | Dessau et al. |
| 5,334,795 | A | 8/1994 | Chu et al. |
| 5,362,697 | A | 11/1994 | Fung et al. |
| 5,384,296 | A | 1/1995 | Tsao |
| 5,488,194 | A | 1/1996 | Beck et al. |
| 5,554,274 | A | 9/1996 | Degnan et al. |
| 5,557,024 | A | 9/1996 | Cheng et al. |
| 5,705,729 | A | 1/1998 | Huang |
| 6,037,513 | A | 3/2000 | Chang et al. |
| 6,077,498 | A | 6/2000 | Diaz Cabanas et al. |
| 6,133,470 | A | 10/2000 | Beck et al. |
| 6,489,529 | B1 | 12/2002 | Cheng et al. |
| 6,504,070 | B2 | 1/2003 | Matsumoto et al. |
| 6,506,953 | B1 | 1/2003 | Cheng et al. |
| 6,730,625 | B1 | 5/2004 | Chang et al. |
| 6,781,025 | B2 | 8/2004 | Dandekar et al. |
| 6,936,744 | B1 | 8/2005 | Cheng et al. |
| 6,984,764 | B1 | 1/2006 | Roth et al. |
| 7,488,861 | B2 | 2/2009 | Boyer et al. |
| 7,579,511 | B1 | 8/2009 | Dakka et al. |
| 7,824,277 | B2 | 11/2010 | Bennett et al. |
| 7,910,778 | B2 | 3/2011 | Chen et al. |
| 7,959,899 | B2 | 6/2011 | Roth et al. |
| 2003/0083527 | A1 | 5/2003 | Kuhnle et al. |
| 2004/0092757 | A1 | 5/2004 | Oguchi et al. |
| 2005/0158238 | A1 | 7/2005 | Tatsumi et al. |
| 2008/0027256 | A1 | 1/2008 | Roth et al. |
| 2008/0027259 | A1 | 1/2008 | Roth et al. |
| 2008/0045768 | A1 | 2/2008 | Roth et al. |
| 2011/0037022 | A1 | 2/2011 | Dakka et al. |

FOREIGN PATENT DOCUMENTS

| | | |
|---|---|---|
| EP | 0 338 734 | 10/1989 |
| JP | 2005-342644 | 12/2005 |
| WO | 95/31421 | 11/1995 |
| WO | 97/17290 | 5/1997 |
| WO | 01/53236 | 7/2001 |
| WO | 01/74767 | 10/2001 |
| WO | 2005/118476 | 12/2005 |
| WO | WO 2006/015824 | 2/2006 |
| WO | WO 2006/015825 | 2/2006 |
| WO | WO 2006/015826 | 2/2006 |
| WO | 2009/038900 | 3/2009 |
| WO | 2009/131769 | 10/2009 |

OTHER PUBLICATIONS

J. Ruan et al., "Structure Elucidation of the Highly Active Titanosilicate Catalyst Ti-YNU-1", Angew. Chem. Int. Ed., 2005, vol. 44, pp. 6719-6723.

L. Slaugh et al., "Hydrodimerization of Benzene to Phenylcyclohexane over Supported Transition Metal Catalysts", Journal of Catalysis, 1969, vol. 13, pp. 385-396.

P. Wu et al., "Methodology for Synthesizing Crystalline Metal-losilicates with Expanded Pore Windows Through Molecular Alkoxysilylation of Zeolitic Lamellar Precursors", Journal of American Chemical Soc., 2008, vol. 130, pp. 8178-8187.

L. Zhicheng et al., "Static Synthesis of High-Quality MCM-22 Zeolite with High $SiO_2/Al_2O_3$ Ratio", Chinese Science Bull, 2004, vol. 49, No. 6, pp. 556-561.

Meier et al., "Atlas of Zeolite Framework Types", Elsevier, Fifth Edition, 2001.

C. Baerlocher et al., "Charge Flipping Combined With Histogram Matching to Solve Complex Crystal Structures From Powder Diffraction Data", Z. Kristallogr., vol. 222, pp. 47-53 (2007).

W. Fan et al., "A Titanosilicate That is Structurally Analogous to an MWW-Type Lamellar Precursor", Angew. Chem. Int. Ed., vol. 43, pp. 236-240 (2004).

C. Gilmore et al., "A Multisolution Method of Phase Determination by Combined Maximization of Entropy and Likelihood. II. Application to Small Molecules", Acta Cryst., A46, pp. 297-308 (1990).

C. Gilmore et al., "A Multisolution Method of Phase Determination by combined Maximization of Entropy and Likelihood. VI. The Use of Error-Correcting Codes as a Source of Phase Permutation and Their Application to the Phase Problem in Powder, Electron and Macromolecular Crystallography", Acta Cryst., A55, pp. 70-83 (1999).

C. Gilmore et al., "Applications of the Maximum Entropy Method to Powder Diffraction and Electron Crystallography", Proc. R. Soc., London, vol. 442, pp. 97-111 (1993).

S. Hovmoller et al., "CRISP: Crystallographic Image Processing on a Personal Computer", Ultramicroscopy, vol. 41, pp, 121-135 (1992).

Z. Liu et al., "Static Synthesis of High-Quality MCM-22 Zeolite With High Si02/A1203 Ratio", Chinese Science Bulletin, vol. 49, No. 6, pp. 556-561 (2004).

J. Raun et al., "Structure Investigation of Novel 3-D Crystalline Silicates From Layered Precursors," 15 IZC Conference, Beijing, Book of Abstracts (2007).

R. Vincent et al., "Double Conical Beam-Rocking System for Measurement of Integrated Electron Diffraction Intensities", Ultramicroscopy, vol. 53, pp. 271-282 (1994).

R. Young, "The Rietveld Method", Oxford Univ. Press, Oxford, pp. 11 (1995).

"Periodic Table of the Elements", Chemical and Engineering News, vol. 63, No. 5, pp. 27 (1995).

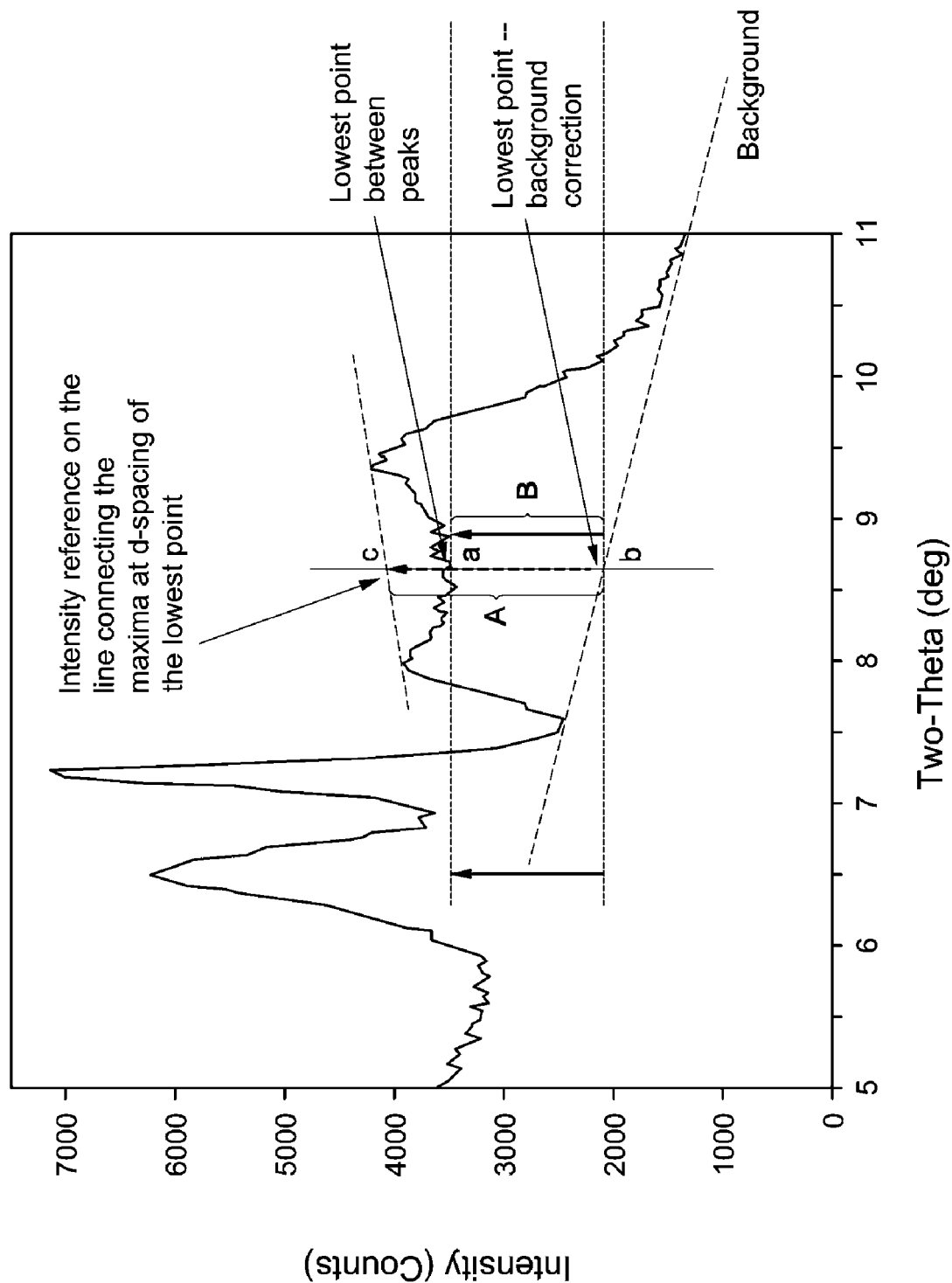

HYDROALKYLATION OF AROMATIC COMPOUNDS USING EMM-13

PRIORITY CLAIM

This application claims the benefit of prior U.S. provisional application Ser. No. 61/084,171 filed Jul. 28, 2008, and International Patent Cooperation Treaty Application No. PCT/US2009/50717, filed Jul. 15, 2009, both of which are hereby incorporated by reference in their entirety.

FIELD OF THE INVENTION

The present disclosure relates to a process for the hydroalkylation of aromatic compounds and particularly to a process for the hydroalkylation of benzene to produce cyclohexylbenzene, using a molecular sieve composition designated as EMM-13 which is an MCM-22 family material having unique XRD features.

BACKGROUND OF THIS DISCLOSURE

Molecular sieve materials, both natural and synthetic, have been demonstrated in the past to have catalytic properties for various types of hydrocarbon conversion. Molecular sieves that find application in catalysis include any of the naturally occurring or synthetic crystalline molecular sieves. Examples of these zeolites include large pore zeolites, intermediate pore size zeolites, and small pore zeolites. These zeolites and their isotypes are described in "Atlas of Zeolite Framework Types", eds. W. H. Meier, D. H. Olson and Ch. Baerlocher, Elsevier, Fifth Edition, 2001, which is hereby incorporated by reference. A large pore zeolite generally has a pore size at least about 7 Å and includes LTL, VFI, MAZ, FAU, OFF, *BEA, and MOR framework type zeolites (IUPAC Commission of Zeolite Nomenclature). Examples of large pore zeolites include mazzite, offretite, zeolite L, VPI-5, zeolite Y, zeolite X, omega, and Beta. An intermediate pore size zeolite generally has a pore size from about 5 Å to less than about 7 Å and includes, for example, MFI, MEL, EUO, MTT, MFS, AEL, AFO, HEU, FER, MWW, and TON framework type zeolites (IUPAC Commission of Zeolite Nomenclature). Examples of intermediate pore size zeolites include ZSM-5, ZSM-11, ZSM-22, MCM-22, silicalite 1, and silicalite 2. A small pore size zeolite has a pore size from about 3 Å to less than about 5.0 Å and includes, for example, CHA, ERI, KFI, LEV, SOD, and LTA framework type zeolites (IUPAC Commission of Zeolite Nomenclature). Examples of small pore zeolites include ZK-4, ZSM-2, SAPO-34, SAPO-35, ZK-14, SAPO-42, ZK-21, ZK-22, ZK-5, ZK-20, zeolite A, chabazite, zeolite T, gmelinite, ALPO-17, and clinoptilolite.

U.S. Pat. No. 4,439,409 refers to a crystalline molecular sieve composition of matter named PSH-3 and its synthesis from a reaction mixture for hydrothermal reaction containing hexamethyleneimine, an organic compound which acts as directing agent for synthesis of the MCM-56 (U.S. Pat. No. 5,362,697). Hexamethyleneimine is also taught for use in synthesis of crystalline molecular sieves MCM-22 (U.S. Pat. No. 4,954,325) and MCM-49 (U.S. Pat. No. 5,236,575). A molecular sieve composition of matter referred to as zeolite SSZ-25 (U.S. Patent No. 4,826,667) is synthesized from a reaction mixture for hydrothermal reaction containing an adamantane quaternary ammonium ion. U.S. Pat. No. 6,077,498 refers to a crystalline molecular sieve composition of matter named ITQ-1 and its synthesis from a reaction mixture for hydrothermal reaction containing one or a plurality of organic additives.

U.S. patent application No. 11/823,129 discloses a novel molecular sieve composition designated as EMM-10-P, having, in its as-synthesized form, an X-ray diffraction pattern including d-spacing maxima at 13.18±0.25 and 12.33±0.23 Angstroms, wherein the peak intensity of the d-spacing maximum at 13.18±0.25 Angstroms is at least as great as 90% of the peak intensity of the d-spacing maximum at 12.33±0.23 Angstroms. U.S. patent application No. 11/824,742 discloses a novel molecular sieve composition designated as EMM-10, in its ammonium exchanged form or in its calcined form, comprising unit cells with MWW topology, said crystalline molecular sieve is characterized by diffraction streaking from the unit cell arrangement in the c direction. The crystalline molecular sieve is further characterized by the arced hk0 patterns of electron diffraction pattern. The crystalline molecular sieve is further characterized by the streaks in the electron diffraction pattern along the c* direction. U.S. patent application No. 11/827,953 discloses a novel crystalline MCM-22 family molecular sieve having, in its as-synthesized form, an X-ray diffraction pattern including a peak at d-spacing maximum of 12.33±0.23 Angstroms, a distinguishable peak at a d-spacing maximum between 12.57 to about 14.17 Angstroms and a non-discrete peak at a d-spacing maximum between 8.8 to 11.0 Angstroms, wherein the peak intensity of the d-spacing maximum between 12.57 to about 14.17 Angstroms is less than 90% of the peak intensity of the d-spacing maximum at 12.33±0.23 Angstroms.

The term "MCM-22 family material" (or "material of the MCM-22 family" or "molecular sieve of the MCM-22 family"), as used herein, includes:

(i) molecular sieves made from a common first degree crystalline building block "unit cell having the MWW framework topology". A unit cell is a spatial arrangement of atoms which is tiled in three-dimensional space to describe the crystal as described in the "Atlas of Zeolite Framework Types", Fifth edition, 2001, the entire content of which is incorporated as reference;

(ii) molecular sieves made from a common second degree building block, a 2-dimensional tiling of such MWW framework type unit cells, forming a "monolayer of one unit cell thickness", preferably one c-unit cell thickness;

(iii) molecular sieves made from common second degree building blocks, "layers of one or more than one unit cell thickness", wherein the layer of more than one unit cell thickness is made from stacking, packing, or binding at least two monolayers of one unit cell thick of unit cells having the MWW framework topology. The stacking of such second degree building blocks can be in a regular fashion, an irregular fashion, a random fashion, or any combination thereof; or (iv) molecular sieves made by any regular or random 2-dimensional or 3-dimensional combination of unit cells having the MWW framework topology.

The MCM-22 family materials are characterized by having an X-ray diffraction pattern including d-spacing maxima at 12.4±0.25, 3.57±0.07 and 3.42±0.07 Angstroms (either calcined or as-synthesized). The MCM-22 family materials may also be characterized by having an X-ray diffraction pattern including d-spacing maxima at 12.4±0.25, 6.9±0.15, 3.57±0.07 and 3.42±0.07 Angstroms (either calcined or as-synthesized). The X-ray diffraction data used to characterize the molecular sieve are obtained by standard techniques using the K-alpha doublet of copper as the incident radiation and a diffractometer equipped with a scintillation counter and associated computer as the collection system. Materials belong to the MCM-22 family include MCM-22 (described in U.S. Pat. No. 4,954,325), PSH-3 (described in U.S. Pat. No. 4,439, 409), SSZ-25 (described in U.S. Pat. No. 4,826,667), ERB-1 (described in European Patent No. 0293032), ITQ-1 (described in U.S. Pat. No. 6,077, 498), ITQ-2 (described in International Patent Publication No. WO97/17290), ITQ-30 (described in International Patent Publication No. WO2005118476), MCM-36 (described in U.S. Pat. No. 5,250,277), MCM-49 (described in U.S. Pat. No. 5,236,575) and MCM-56 (described in U.S. Pat. No. 5,362,697). The entire contents of the patents are incorporated herein by reference.

It is to be appreciated the MCM-22 family molecular sieves described above are distinguished from conventional large pore zeolite alkylation catalysts, such as mordenite, in that the MCM-22 materials have 12-ring surface pockets which do not communicate with the 10-ring internal pore system of the molecular sieve.

The zeolitic materials designated by the IZA-SC as being of the MWW topology are multi-layered materials which have two pore systems arising from the presence of both 10 and 12 membered rings. The Atlas of Zeolite Framework Types classes five differently named materials as having this same topology: MCM-22, ERB-1, ITQ-1, PSH-3, and SSZ-25.

The MCM-22 family molecular sieves have been found to be useful in a variety of hydrocarbon conversion processes. Examples of MCM-22 family molecular sieve are MCM-22, MCM-49, MCM-56, ITQ-1, PSH-3, SSZ-25, and ERB-1. Such molecular sieves are useful for alkylation of aromatic compounds. For example, U.S. Pat. No. 6,936,744 discloses a process for producing a mono-alkylaromatic aromatic compound, particularly cumene, comprising the step of contacting a polyalkylated aromatic compound with an alkylatable aromatic compound under at least partial liquid phase conditions and in the presence of a transalkylation catalyst to produce the mono-alkylaromatic aromatic compound, wherein the transalkylation catalyst comprises a mixture at least two different crystalline molecular sieves, wherein each of the molecular sieves is selected from zeolite beta, zeolite Y, mordenite and a material having an X-ray diffraction pattern including d-spacing maxima at 12.4±0.25, 6.9±0.15, 3.57±0.07 and 3.42±0.07 Angstroms.

A report by J. Ruan, P. Wu, B. Slater, L. Wu, J. Xiao, Y. Liu, M. He, O. Terasaki at the 15 IZA Conference in Beijing in 2007 disclosed ISE-MWW and ISE-FER materials, the former made from MCM-22-P material as starting material. U.S. Patent Application Publication 2005/0158238 to Tatsumi et al. disclosed MWW type zeolite substance. U.S. Patent Application Publication 2004/0092757 to Oguchi et al. disclosed crystalline MWW type titanosilicate catalyst. A report by W. Fan, P. Wu, S. Namba, and T. Tatsumi (J. Catalyst 243 (2006) 183-191) disclosed a new titanosilicate molecular sieve with the structure analogous to MWW-type lamellar precursor. J. Ruan, P. Wu B. Slater and 0. Terasaki disclosed detailed structure of Ti-YNU-1 (Angew. Chem. Int. Ed., 2005, 44, 6719) similar to ISE-MWW. Another report by P. Wu, J. Ruan, L. Wang, L. Wu, Y. Wang, Y. Liu, W. Fan. M. He, O. Terasaki and T. Tatsumi disclosed a methodology for synthesizing crystalline aluminosilicates with expanded pore windows through molecular alkoxysilylation of zeolitic lamellar precursors (J. Am. Chem. Soc. 2008, 130, 8178-8187).

It is known that crystal morphology, size and aggregation/agglomeration, or new x-ray diffraction can affect catalyst behavior, especially regarding catalyst activity and stability.

It has been known for many years that cyclohexylbenzene can be produced from benzene by the process of hydroalkylation or reductive alkylation. In this process, benzene is heated with hydrogen in the presence of a catalyst such that the benzene undergoes partial hydrogenation to produce cyclohexene which then alkylates the benzene starting material. Thus U.S. Pat. Nos. 4,094,918 and 4,177,165 disclose hydroalkylation of aromatic compounds over catalysts which comprise nickel- and rare earth-treated zeolites and a palladium promoter. Similarly, U.S. Pat. Nos. 4,122,125 and 4,206,082 disclose the use of ruthenium and nickel compounds supported on rare earth-treated zeolites as aromatic hydroalkylation catalysts. The zeolites employed in these prior art processes are zeolites X and Y. In addition, U.S. Pat. No. 5,053,571 proposes the use of ruthenium and nickel supported on zeolite beta as the aromatic hydroalkylation catalyst. However, these earlier proposals for the hydroalkylation of benzene suffer from the problems that the selectivity to cyclohexylbenzene is low, particularly at economically viable benzene conversion rates, and that large quantities of unwanted by-products, particularly cyclohexane and methylcyclopentane, are produced.

More recently, U.S. Pat. No. 6,037,513 has disclosed that cyclohexylbenzene selectivity in the hydroalkylation of benzene can be improved by contacting the benzene and hydrogen with a bifunctional catalyst comprising at least one hydrogenation metal and a molecular sieve of the MCM-22 family. The hydrogenation metal is preferably selected from palladium, ruthenium, nickel, cobalt and mixtures thereof and the contacting step is conducted at a temperature of about 50 to 350° C., a pressure of about 100 to 7000 kPa, a benzene to hydrogen molar ratio of about 0.01 to 100 and a WHSV of about 0.01 to 100. The '513 patent discloses that the resultant cyclohexylbenzene can then be oxidized to the corresponding hydroperoxide and the peroxide decomposed to the desired phenol and cyclohexanone.

According to the present invention, it has now been found the hydroalkylation of an aromatic compound over a bifunctional catalyst comprising a EMM-13 zeolite and at least one hydrogenation metal yields a favorable ratio of the produced monocycloalkyl-substituted aromatic compound to the produced di-cycloalkyl-substituted aromatic compound. Although the di-cycloalkyl-substituted aromatic compound can be transalkylated back to corresponding mono-cycloalkyl-substituted aromatic compound, the cost of transalkylation is not insignificant.

There is, therefore, a need for a new process of producing cycloalkyl-substituted aromatic compounds, especially mono-cylcoalkyl-substituted aromatic compounds, with crystalline molecular sieve.

SUMMARY OF THIS DISCLOSURE

In some embodiments, this disclosure relates to a hydroalkylation process of producing mono-cycloalkyl-substituted aromatic compounds using a catalyst system comprising a molecular sieve and at least one hydrogenation metal having hydrogentation activity, wherein the molecular sieve has, in its as-synthesized form, and in calcined form, an X-ray diffraction pattern including peaks having a d-spacing maximum in the range of 14.17 to 12.57 Angstroms (~6.15-7.05 deg 2-θ), a d-spacing maximum in the range of 12.1 to 12.56 Angstroms (~7.3-7.05 deg 2-θ), a d-spacing maximum in the range of 10.14 to 12.0 Angstroms (8.7-7.35 deg 2-θ), and a d-spacing maximum in the range from 8.66 to 10.13 Angstroms (10.2-8.7 deg 2-θ); wherein said peaks having d-spacing maximum in the range of 10.14 to 12.0 Angstroms (8.7-7.35 deg 2-θ) and d-spacing maximum in the range from 8.66 to 10.13 Angstroms (10.2-8.7 deg 2-θ) exhibit a valley in between, wherein the measured intensity corrected for background at the lowest point of said valley is less than 50% of the intensity point at the same XRD d-spacing on the line connecting said peaks having d-spacing maxima in the range of 10.14 to 12.0 Angstroms (8.7-7.35 deg 2-θ) and in the range from 8.66 to 10.13 Angstroms (10.2-8.7 deg 2-θ); wherein said molecular sieve has less than 1.6 wt % Ti.

In some embodiments, this disclosure relates to a hydroalkylation process of producing mono-cycloalkyl-substituted aromatic compounds using a catalyst comprising a molecular sieve and at least one hydrogenation metal having hydrogenation activity, wherein the molecular sieve has, in its as-synthesized form and in calcined form, an X-ray diffraction pattern including peaks at d-spacing maxima at 13.18±0.25, 12.33±0.23, 11.06±0.18 and 9.25±0.13 Angstroms, wherein said peaks at 11.06±0.18 and 9.25±0.13 Angstroms exhibit a valley in between the 11.06±0.18 and 9.25±0.13 Angstroms but with measured intensity corrected for background at the lowest point being less than 50% of the intensity point at the same XRD d-spacing on the line connecting d-spacing maxima at 11.06±0.18 and 9.25±0.13 Angstroms; wherein said molecular sieve has less than 1.6 wt % Ti.

In other embodiments, the aromatic compound is benzene and the corresponding mono-cycloalkyl-substituted aromatic compounds are cyclohexylbenzene.

In yet other embodiments, the process of this disclosure comprises contacting an aromatic compound with hydrogen in the presence of a catalyst system comprising (i) a molecular sieve; (ii) an inorganic oxide different from the molecular sieve; and (iii) at least one hydrogenation metal under hydroalkylation conditions to form mono-cycloalkyl-substituted aromatic compounds.

In other embodiments, the as-synthesized crystalline molecular sieve is further calcined under calcination conditions to form calcined molecular sieve, wherein the calcination conditions comprise a temperature in the range of 300 to 700° C. for a time in the range of 1 min to 500 hours.

In some aspects, the molecular sieve further comprises, in its as-synthesized form and in calcined form, an X-ray diffraction pattern including peaks at 3.57±0.07 and 3.42±0.07 Angstroms.

In other aspects, the molecular sieve further comprises, in its as-synthesized form and in calcined form, an X-ray diffraction pattern including peak at 6.9±0.15.

In yet other aspects, the calcined molecular sieve has a composition involving the molar relationship:

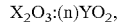

$X_2O_3:(n)YO_2$, wherein X is a trivalent element comprises at least one of aluminum, boron, iron and gallium, Y is a tetravalent element comprises at least one of silicon and germanium, and n is at least about 10. In the as-synthesized form the molecular sieve has a formula, on an anhydrous basis and in terms of moles of oxides per n moles of $YO_2$, as follows:

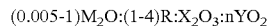

$(0.005-1)M_2O:(1-4)R:X_2O_3:nYO_2$ wherein M is an alkali or alkaline earth metal, and R is an organic moiety. In a preferred embodiment, n is from about 10 to about 150, more preferably from about 30 to about 60. In some preferred embodiment, X is aluminum and Y is silicon.

In some embodiments, the calcined molecular sieve has a collidine adsorption capacity at least 150 μmoles/g, preferably at least 250 μmoles/g.

In a further embodiment, this disclosure relates to a catalyst system comprising (i) a molecular sieve having, in its as-synthesized form and in calcined form, an X-ray diffraction pattern including peaks having a d-spacing maximum in the range of 14.17 to 12.57 Angstroms, a d-spacing maximum in the range of 12.1 to 12.56 Angstroms, and non-discrete scattering between about 8.85 to 11.05 Angstroms or exhibit a valley in between the peaks having a d-spacing maximum in the range of 10.14 to 12.0 Angstroms and a d-spacing maximum in the range from 8.66 to 10.13 Angstroms with measured intensity corrected for background at the lowest point being not less than 50% of the point at the same XRD d-spacing on the line connecting maxima in the range of 10.14 to 12.0 Angstroms and in the range from 8.66 to 10.13 Angstroms; (ii) an inorganic oxide different from said molecular sieve; and (iii) at least one hydrogenation metal wherein at least a portion of the hydrogenation metal is supported on the inorganic oxide in (ii).

These and other facets of the present invention shall become apparent from the following detailed description, Figures, and appended claims.

BRIEF DESCRIPTION OF THE FIGURE

FIG. 1 shows the XRD pattern between 5 to 11 degree 2-θ of Example 1.

DETAILED DESCRIPTION

Introduction

Described herein is a process for the hydroalkylation of aromatic compounds, particularly benzene, to produce cycloalkyl-substituted aromatic compounds. Insofar as the hydroalkylation step produces di-cycloalkyl-substituted aromatic compounds (e.g. dicyclohexylbenzene) in addition to the desired mono-cycloalkyl-substituted aromatic compound product (e.g. mono-cyclohexylbenzene), the process can include the further step of transalkylating the di-cycloalkyl-substituted aromatic compounds with additional aromatic compounds (e.g. benzene) to produce additional mono-cycloalkyl-substituted aromatic compound product.

All patents, patent applications, test procedures (such as ASTM methods, UL methods, and the like), priority documents, articles, publications, manuals, and other documents cited herein are fully incorporated by reference to the extent such disclosure is not inconsistent with the present invention and for all jurisdictions in which such incorporation is permitted.

When numerical lower limits and numerical upper limits are listed herein, ranges from any lower limit to any upper limit are contemplated. While the illustrative embodiments of the disclosure have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside in the present disclosure, including all features which would be treated as equivalents thereof by those skilled in the art to which the disclosure pertains.

As used in this specification, the term "framework type" is used in the sense described in the "Atlas of Zeolite Framework Types," 2001.

As used herein, the numbering scheme for the Periodic Table Groups is used as in Chemical and Engineering News, 63(5), 27 (1985).

The present invention encompasses the hydroalkylation of any aromatic compounds, however, the details of benzene alkylation are presented below as a specific example. It is to be understood that all embodiments useful for benzene hydroalkylation are also useful in the hydroalkylation of other aromatic compounds.

Hydroalkylation Process

The term "aromatic" in reference to the aromatic compounds which may be useful as feedstock herein is to be understood in accordance with its art-recognized scope. This includes alkyl substituted and unsubstituted mono- and polynuclear compounds. Compounds of an aromatic character that possess a heteroatom may also be useful provided sufficient catalytic activity is maintained under the reaction conditions selected.

Substituted aromatic compounds that can be hydroalkylated herein must possess at least one hydrogen atom directly bonded to the aromatic nucleus. The aromatic rings can be substituted with one or more alkyl, aryl, alkaryl, alkoxy, aryloxy, cycloalkyl, halide, and/or other groups that do not interfere with the hydroalkylation reaction.

Suitable aromatic compounds include benzene, naphthalene, anthracene, naphthacene, perylene, coronene, and phenanthrene, with benzene being preferred.

In another embodiment, the aromatic compound is selected from the group consisting of benzene, naphthalene, anthracene, naphthacene, perylene, coronene, phenanthrene, xylene, n-propylbenzene, alpha-methylnaphthalene, o-diethylbenzene, m-diethylbenzene, p-diethylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; 3-methyl-phenanthrene and mixtures thereof The first step in the present process comprises contacting an aromatic compound (e.g. benzene) with hydrogen under hydroalkylation conditions in the presence of a hydroalkylation catalyst whereby the in the case of benzene, the aromatic compound undergoes the following reaction to produce cyclohexylbenzene (CHB):

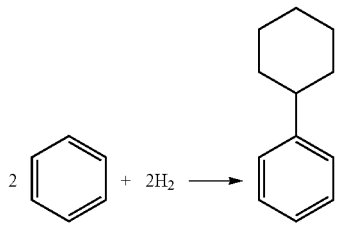

In the case of benzene hydroalkylation, competing reactions include the complete saturation of the benzene to produce cyclohexane, dialkylation to produce dicyclohexylbenzene and reorganization/alkylation reactions to produce impurities, such as methylcyclopentylbenzene (MCPB). Although dicyclohexylbenzene can be transalkylated to produce additional CHB product, conversion to cyclohexane represents loss of valuable feed, whereas impurities such as methylcyclopentylbenzene (MCPB) are particularly undesirable since the boiling point of MCPB is very close to that of CHB so that it is very difficult to separate MCPB from CHB. It is therefore important to minimize the production of MCPB impurity in the hydroalkylation reaction.

Preferably, the hydroalkylation reaction yields a ratio of mono-cycloalkyl-substituted aromatic compound to di-cycloalkyl-substituted aromatic comound from greater than about 10, about 15, about 20, about 25, about 40, about 50, about 60, about 70, and about 80. For example, in the case of benzene hydroalkylation, the reaction yields a ratio of cyclohexylbenzene to dicyclohexylbenzene of from greater than about 10, about 15, about 20, about 25, about 40, about 50, about 60, about 70, and about 80.

Any commercially available benzene feed can be used in the hydroalkylation step, but preferably the benzene has a purity level of at least 99 wt %. Similarly, although the source of hydrogen is not critical, it is generally desirable that the hydrogen is at least 99 wt % pure.

Preferably, the total feed to the hydroalkylation step contains less than 1000 ppm, such as less than 500 ppm, for example less than 100 ppm, water. Preferably, the total feed typically contains less than 100 ppm, such as less than 30 ppm, for example less than 3 ppm, sulfur. Preferably, the total feed contains less than 10 ppm, such as less than 1 ppm, for example less than 0.1 ppm, nitrogen. In a particularly preferred embodiment at least two, and preferably all three of the above mentioned preferred levels for water, sulfur and nitrogen are achieved.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Irrespective of whether the hydrogen is fed to the reaction continuously or in stages, it is important that the ratio of the total number of moles of hydrogen fed to the reaction to the number of moles of benzene fed to the reaction is between 0.4 and 0.9:1, such as between about 0.5 and about 0.8:1, for example between about 0.6 and about 0.7:1.

Suitable temperatures for conducting the hydroalkylation reaction are between about 100° C. and about 400° C., such as between about 125° C. and about 250° C. Suitable reaction pressures are between about 100 and about 7,000 kPaa, such as between about 500 and about 5,000 kPa-a. Suitable feed weight hourly space velocity (WHSV) based on benzene of from about 0.01 to 250 hr$^{-1}$, from about 0.1 to about 50 hr$^{-1}$, from about 0.1 to about 5.0 hr$^{-1}$, and from about 0.2 to about 1.5 hr$^{-1}$.

The catalyst employed in the hydroalkylation reaction is a bifunctional catalyst comprising a molecular sieve of EMM-13 described herein and at least one hydrogenation metal.

Any known hydrogenation metal can be employed in the present hydroalkylation catalyst although suitable metals for the first hydrogenation metal include palladium, ruthenium, nickel, zinc, tin, and cobalt, with palladium being particularly advantageous. Generally, the amount of hydrogenation metal present in the catalyst is between about 0.05 and about 10 wt %, such as between about 0.1 and about 5 wt %, of the catalyst. In one embodiment, where the EMM-13 is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The catalyst preferably contains a second hydrogenation metal component, in addition to and different from the hydrogenation metal, which acts to promote the hydrogenation function of the catalyst. Suitable second hydrogenation metal components are selected from zinc, tin, nickel, cobalt and mixtures thereof. Again, the amount of second metal component present in the catalyst may vary significantly but preferably the amount of the second hydrogenation metal present in the catalyst is between about 0.05 and about 10 wt %, such as between about 0.1 and about 5 wt %, of the catalyst.

The hydrogenation metal may be directly supported on the EMM-13 molecular sieve by, for example, impregnation or ion exchange. However, in a more preferred embodiment, at least a portion, for example at least 50 wt %, at least 75wt %, and generally substantially all of the at least one hydrogenation metal is supported on an inorganic oxide separate from but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13 and 14 of the Periodic Table of Elements, such as alumina and/or titania and/or zirconia. As used herein, the numbering scheme for the Periodic Table Groups is as disclosed in Chemical and Engineering News, 63(5), 27 (1985). When the catalyst system comprises a composite of the molecular sieve and the inorganic oxide that is different from the molecular sieve, these two components are conveniently present in a weight ratio in the range 90:10 to 10:90, such as 80:20 to 20:80, for example 70:30 to 30:70 or 60:40 to 40:60.

In the above-mentioned preferred embodiment, the hydrogenation metal is deposited on the inorganic oxide, conveniently by impregnation, before the metal-containing inorganic oxide is composited with the molecular sieve. Typically, the catalyst composite is produced by co-pelletization, in which a mixture of the molecular sieve and the metal-containing inorganic oxide are formed into pellets at high pressure (generally about 350 to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Although the hydroalkylation step is highly selective towards mono-cycloalkyl-substituted aromatic compound products (e.g. cyclohexylbenzene), the effluent from the hydroalkylation reaction will normally contain some dialkylated products, as well as unreacted aromatic feed and the desired monoalkylated species. The unreacted aromatic feed is normally recovered by distillation and recycled to the alkylation reactor. In the case of benzene hydroalkylation, for example, the bottoms from the distillation are further distilled to separate the monocyclohexylbenzene product from any dicyclohexylbenzene and other heavies. Depending on the amount of dicyclohexylbenzene present in the reaction effluent, it may be desirable to transalkylate the dicyclohexylbenzene with additional benzene to maximize the production of the desired monoalkylated species.

Transalkylation with additional aromatic compound (e.g. benzene) is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y or mordenite. The transalkylation reaction is typically conducted under at least partial liquid phase conditions, which suitably include a temperature of about 100 to about 300° C. and/or a pressure of about 800 to about 3500 kPa and/or a weight hourly space velocity of about 1 to about 10 $hr^{-1}$ on total feed and/or a mono-cycloalkyl-substituted aromatic compound/di-cycloalkyl-substituted aromatic compound weight ratio about of 1:1 to about 5:1.

X-Ray Powder Diffraction Pattern for EMM-13

The interplanar spacings, d's, were calculated in Angstrom units (Å), and the relative intensities of the lines, $I/I_o$, where the intensity of the strongest line above background, $I_o$, is counted as 100, were derived with the use of a profile fitting routine (or second derivative algorithm). The intensities are uncorrected for Lorentz and polarization effects. The relative intensities are given in terms of the symbols VS=very strong (greater than 60 to 100), S=strong (greater than 40 to 60), M=medium (greater than 20 to 40) and W=weak (0 to 20). It should be understood that diffraction data listed as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the structure. These minor effects, including changes in relative intensities, can also occur as a result of differences in cation content, framework composition, nature and degree of pore filling, and thermal and/or hydrothermal history. Other changes in diffraction patterns can be indicative of important differences between materials, which is the case for comparing MCM-22 with similar materials, e.g., MCM-49, MCM-56, and PSH-3.

The interplanar spacings, d's, were considered broad if they exhibited peak width of about 1.5° or more at half height determined as 50% intensity value from the peak maximum to the baseline.

The term "XRD distinguishable peak" as used herein is defined as XRD peak with clearly defined peak maximum, which is at least two times of the average background noise level.

The term "non-discrete" peaks (also "unresolved" peaks) in XRD as used herein means peaks having a monotonic profile in-between them (successive points either consistently increasing (or staying even) or decreasing (or staying even) within noise).

The term "discrete" peaks (also "resolved" peaks) in XRD as used herein means XRD peak(s) which are not non-discrete (unresolved).

FIG. 1 graphically demonstrates the XRD pattern between 5 to 11 degree 2-θ of the product of Example 1. The measured intensity corrected for background at the lowest point between d-spacing maxima in the range of 10.14 to 12.0 Angstroms and in the range from 8.66 to 10.13 Angstroms, represented as B, is the distance between the lowest point (point a) and the point (point b) on the line of the background correction line at the same XRD d-spacing of the lowest point (point a). The distance between the point b and the point (point c) on the line connecting d-spacing maxima in the range of 10.14 to 12.0 Angstroms and in the range from 8.66 to 10.13 Angstroms at the same XRD d-spacing of the lowest point is represented as A.

Composition Matter of EMM-13

EMM-13 is a new MCM-22 family material with unprecedented XRD pattern indicating expanded structure and increased access to the interlayer region. It shows a unique distinctive combination of XRD features in the calcined form comprising peaks having a d-spacing maximum in the range of 14.17 to 12.57 Angstroms (~6.15-7.05 deg 2-θ), a d-spacing maximum in the range of 12.1 to 12.56 Angstroms (~7.3-7.05 deg 2-θ), a d-spacing maximum in the range of 10.14 to 12.0 Angstroms (8.7-7.35 deg 2-θ), and a d-spacing maximum in the range from 8.66 to 10.13 Angstroms (10.2-8.7 deg 2-θ); wherein said peaks having d-spacing maximum in the range of 10.14 to 12.0 Angstroms (8.7-7.35 deg 2-θ) and d-spacing maximum in the range from 8.66 to 10.13 Angstroms (10.2-8.7 deg 2-θ) exhibit a valley in between, wherein the measured intensity corrected for background at the lowest point of said valley is less than 50% of the intensity point at the same XRD d-spacing on the line connecting said peaks having d-spacing maxima in the range of 10.14 to 12.0 Angstroms (8.7-7.35 deg 2-θ) and in the range from 8.66 to 10.13 Angstroms (10.2-8.7 deg 2-θ) said EMM-13 molecular sieve has less than 1.6 wt % Ti.

In some embodiments, the composition matter of EMM-13 has, in as-synthesized form and in calcined form, an X-ray diffraction pattern including peaks at d-spacing maxima at 13.5±0.5, 12.33±0.23, and exhibit a valley in between the peaks at 11.05±0.2 and 9.31±0.2 Angstroms with measured intensity corrected for background at the lowest point being less than 50% of the point at the same XRD d-spacing on the line connecting d-spacing maxima at around 11.05±0.2 and 9.31±0.2 Angstroms, wherein said EMM-13 molecular sieve has less than 1.6 wt % Ti.

In further embodiments, the composition matter of EMM-13 further has, in as-synthesized form and in calcined form, an X-ray diffraction pattern including peaks at d-spacing maxima at 3.57±0.06 and 3.43±0.06 Angstroms. In yet further embodiments, the composition matter of EMM-13 further has, in as-synthesized form and in calcined form, an X-ray diffraction pattern including peak at d-spacing maximum at 6.9±0.15 Angstroms. In yet further embodiments, the composition matter of EMM-13 further has, in as-synthesized form and in calcined form, an X-ray diffraction pattern including peak at d-spacing maximum at 3.96±0.08 Angstroms.

In other embodiments, the composition matter of EMM-13 has, in as-synthesized form and in calcined form, an X-ray diffraction pattern including peaks at d-spacing maxima and relative intensities at 13.5±0.5 (M-VS), 12.33±0.23(M-VS), and exhibit a valley in between the peaks at 11.05±0.2 (W-S) and 9.31±0.2 (W-S) Angstroms but with measured intensity corrected for background at the lowest point being less than 50% of the point at the same XRD d-spacing on the line connecting d-spacing maxima at around 11.05±0.2 and 9.31±0.2 Angstroms.

TABLE 1

| Interplanar d-Spacing (Å) | Relative Intensity, I/I$_o$ × 100 |
|---|---|
| 14.17 > d > 12.57 | M-VS |
| 12.56 > d > 12.1 | M-VS |
| 12.0 > d > 10.14 | W-S |
| 10.13 > d > 8.66 | W-S |
| 6.9 ± 0.15 | W-M, broad |
| 3.96 ± 0.08 | W-VS, broad |
| 3.57 ± 0.06 | W-M |
| 3.43 ± 0.06 | M-VS |

In other embodiments, the composition matter of EMM-13 further has, in as-synthesized form and in calcined form, an X-ray diffraction pattern including peaks at d-spacing maxima at 3.57±0.06 (W-M) and 3.43±0.06 (M-VS) Angstroms. In yet further embodiments, the composition matter of EMM-13 further has, in as-synthesized form and in calcined form, an X-ray diffraction pattern including peak at d-spacing maximum at 6.9±0.15 Angstroms (W-M, broad). In yet further embodiments, the composition matter of EMM-13 further has, in as-synthesized form and in calcined form, an X-ray diffraction pattern including peak at d-spacing maximum at 3.96±0.08 Angstroms (W-VS, broad).

In some preferred embodiments, the X-ray diffraction pattern of the crystalline molecular sieve EMM-13 further has peaks at d-spacing maxima and intensities listed in Table 1.

In some embodiments, the X-ray diffraction pattern of the crystalline molecular sieve of this disclosure further includes a d-spacing maximum at 28±1 Angstroms.

In other embodiments, the composition matter of EMM-13 may be defined by its crystal structure. The crystal structure of EMM-13 may be defined by its unit cell, which is the smallest structural unit containing all the structural elements of the material. The unit cell of EMM-13 has P6/mmm space group and atomic coordinates of tetrahedral atoms (T) and oxygen atoms listed in Table 2 and with unit cell dimensions of a=14.198(2) and c=27.647(7) Å, wherein said EMM-13 molecular sieve has less than 1.6 wt % Ti. Since the tetrahedral atoms may move about due to other crystal forces (presence of inorganic or organic species, for example), a range of ±0.05 nm is implied for each coordinate position.

TABLE 2

| Atom | x/a | y/b | z/c | Uiso | occ. |
|---|---|---|---|---|---|
| T1 | 0.6667 | 0.3333 | 0.1126(2) | 0.00649 | 1.0 |
| T2 | 0.4652(5) | 0.2326(3) | 0.1754(3) | | |
| T3 | 0.3901(5) | 0.0 | 0.1897(4) | | |
| T4 | 0.6667 | 0.3333 | 0.2403(4) | | |
| T5 | 0.6667 | 0.3333 | 0.3575(4) | | |
| T6 | 0.3894(5) | 0.0 | 0.3050(4) | | |
| T7 | 0.4215(5) | 0.2108(2) | 0.3593(3) | | |
| T8 | 0.2502(5) | 0.1251(3) | 0.4450(2) | | |
| T9 | 0.6667 | 0.3333 | 0.0 | | |
| O10 | 0.6667 | 0.3333 | 0.0562(1) | 0.010 | 1.0 |
| O11 | 0.5420(3) | 0.2710(1) | 0.1282(2) | | |
| O12 | 0.3876(5) | 0.1037(2) | 0.1681(4) | | |
| O13 | 0.5408(3) | 0.2704(2) | 0.2230(3) | | |
| O14 | 0.6667 | 0.3333 | 0.2991(4) | | |
| O15 | 0.3725(2) | 0.0 | 0.2473(3) | | |
| O16 | 0.5 | 0.0 | 0.176(1) | | |
| O17 | 0.5 | 0.0 | 0.318(1) | | |
| O18 | 0.3951(6) | 0.1062(3) | 0.3279(3) | | |
| O19 | 0.5453(3) | 0.2727(1) | 0.3786(4) | | |
| O20 | 0.3519(7) | 0.1759(4) | 0.4087(3) | | |
| O21 | 0.1806(5) | 0.0 | 0.4320(3) | | |
| O22 | 0.2928(8) | 0.1464(4) | 0.5 | | |
| Extra-framework: | | | | | |
| T23 | 0.4499 | 0.1812 | 0.0686 | 0.025 | 0.355 |
| T24 | 0.2477 | 0.1232 | 0.0360 | 0.025 | 0.160 |
| Approximate | | | | | |
| O25 | 0.663 | 0.452 | 0.0 | 0.025 | 0.099 |

In Table 2, x/a, y/b, z/c are the fractional coordinates of the atoms in the unit cell referred to the unit cell axes a=b, c. Uiso is the isotropic temperature factor for each atom in Å$^2$. The quantity 'occ' is the occupancy factor for each atom, i.e., if less than 1.0, there is a statistical distribution of atoms or vacancies at each locus in the crystal.

In some embodiments, the EMM-13 calcined exhibits an extraordinary high collidine number greater than 150 μmoles/g, preferably greater than 200 μmoles/g, more preferably greater than 250 μmoles/g, even more preferably greater than 300 μmoles/g, and most preferably greater than 350 μmoles/g, compared to about 120-200 μmoles/g for EMM-10 and 120 μmoles/g for MCM-22. Not intended to be limited by any theory, we believe that the EMM-13 calcined has c-unit cell parameter fixed in the expanded form as the precursor when calcined.

Chemical Composition of as-synthesized EMM-13 and Calcined EMM-13

The as-synthesized EMM-13 molecular sieve material of this disclosure may be prepared from an MCM-22-P precursor, which can be obtained from a reaction mixture for hydrothermal reaction containing sources of alkali or alkaline earth metal (M), e.g., sodium or potassium, cation, an oxide of trivalent element X, e.g., aluminum, an oxide of tetravalent element Y, e.g., silicon, an organic (R) directing agent, hereinafter more particularly described, and water, the reaction mixture for hydrothermal reaction having a composition, in terms of mole ratios of oxides:

$YO_2/X_2O_3$ in the range of 10 to infinity or in the range of 10 to 50;

$M/X_2O_3$ in the range of 0.005-5.0; and $R/X_2O_3$ in the range of 0.01-10.

The calcined EMM-13 molecular sieve material of this disclosure may be prepared by calcining as-synthesized EMM-13 under calcination conditions to remove at least the majority of the organic template R from the as-synthesized EMM-13.

The as-synthesized or calcined EMM-13 molecular sieve material has less than 1.6 wt % titanium, preferably less than 1 wt %, more preferably less than 0.5 wt %, and most preferably less than 0.1 wt % of titanium.

Process of Making EMM-13

In some embodiments, this disclosure relates to a method of manufacturing an as-synthesized crystalline molecular sieve EMM-13, the method comprising the steps of:

(a) providing a mixture comprising MCM-22-P and acidic composition, optionally a spacing agent;

(b) treating the mixture at treatment conditions to form a product comprising as-synthesized EMM-13; and (c) recovering the acid treated crystalline molecular sieve.

In some preferred embodiments, the as-synthesized EMM-13 is made by a process comprising:

(1) providing a mixture comprising MCM-22-P having $Si/Al_2$ in the range from 10-infinity, preferable from about 10 to 150, and acidic composition comprising at least one of nitric acid, sulfuric acid, hydrochloric acid; oxalic acid, wherein said acid has a concentration of less than or equal to 10 N, preferably less than 1N, optionally a spacing agent comprising at least one of dimethyldiethoxy silane, diethyldiethoxy silane, and tetraethyl silane (TEOS), preferable TEOS; and (2) treating the mixture of step (1) to treatment conditions, wherein the treatment conditions comprise a temperature in the range of 50-250° C. for a time in the range of 1-24 hrs, optionally with a stirring speed in the range of 0-1000 RPM.

The mixture of step (a) comprises MCM-22-P, acidic composition, and optionally a spacing agent, wherein the weight ratio of the solid content of the MCM-22-P over the acidic composition and the weight ratio of the spacing agent over the solid content of the MCM-22-P are listed in Table 3. The treatment conditions of step (b) include treatment temperature, treatment time. Useful and preferred ranges of the treatment temperature and treatment time are listed in Table 3.

TABLE 3

| | Useful range | Preferred range | Most preferred range |
|---|---|---|---|
| Solid content (wt) Acidic composition | 0.001-1000 | 0.01-100 | 0.1-10 |
| Spacing agent (wt) Solid content (wt) | 0-2 | 0-1 | 0.01-0.5 |
| Acid concentration (N) | 0.001-10 | 0.001-5 | 0.01-2 |
| Temperature (° C.) | 25-250 | 50-200 | 90-170 |
| Time (hr) | 0.01-240 | 1-48 | 1-24 |

The following solid content over acidic composition weight ratios are useful lower limits: 0.001, 0.01, 0.05, 0.1, 0.5, 1, 5, 10, 50, 100 and 500. The following solid content over acidic composition weight ratios are useful upper limits: 0.01, 0.05, 0.1, 0.5, 1, 5, 10, 50, 100, 500 and 1000. The solid content over acidic composition weight ratio falls in a range between any one of the above-mentioned lower limits and any one of the above-mentioned upper limits, so long as the lower limit is less than or equal to the upper limit. The solid content over acidic composition weight ratio may be present in an amount ranging from 0.01 to 100 in one embodiment, alternatively 0.1 to 10, alternatively 0.1 to 5.

The following ratios are useful lower spacing agent over solid content weight ratio limits: 0, 0.001, 0.01, 0.05, 0.1, 0.5, 1, and 1.5. The following ratios are useful upper spacing agent over solid content weight ratio limits: 0.001, 0.01, 0.05, 0.1, 0.5, 1, 1.5, and 2. The spacing agent over solid content weight ratio falls in a range between any one of the above-mentioned lower spacing agent over solid content weight ratio limits and any one of the above-mentioned upper spacing agent over solid content weight ratio limits, so long as the lower spacing agent over solid content weight ratio limit is less than or equal to the upper spacing agent over solid content weight ratio limit. The spacing over solid content weight ratio may be present in an amount ranging from 0 to 2 in one embodiment, alternatively 0 to 1, and alternatively 0.1 to 0.5.

The following temperatures (° C.) are useful lower treatment temperature limits: 25, 50, 60, 70, 80, 90, 100, 110, 120, 130, 140, 150, 160, 170, and 200. The following temperatures (° C.) are useful upper treatment temperature limits: 50, 60, 70, 80, 90, 100, 110, 120, 130, 140, 150, 160, 170, 180, 190, 200, 210, 220, 230, 240, and 250. The treatment temperature (° C.) falls in a range between any one of the above-mentioned lower treatment temperature limits and any one of the above-mentioned upper treatment temperature limits, so long as the lower treatment temperature limit is less than or equal to the upper treatment temperature limit. The treatment temperature may be present in an amount ranging from 25° C. to 250° C. in one embodiment, alternatively 70° C. to 200° C., and alternatively 90° C. to 170° C.

The following times (hr) are useful lower time limits for treatment: 0.01, 1, 5, 10, 20, 30, 50, 100, and 150. The following times (hr) are useful upper time limits for treatment: 1, 5, 10, 20, 40, 50, 70, 100, 150, 200, and 240. The time (hr) for treatment falls in a range between any one of the above-mentioned lower time limits for treatment and any one of the above-mentioned upper time limits for treatment, so long as the lower time limit for treatment is less than or equal to the upper time limit for treatment. The time for treatment may be present in an amount ranging from 1 to 100 in one embodiment, alternatively 1 to 48, and alternatively 1 to 24.

(1) MCM-22-P

The MCM-22-P product is disclosed in U.S. Pat. No. 4,954,325. The entirety of which is incorporated herein by reference.

The MCM-22-P as disclosed by U.S. Pat. No. 4,954,325, may be made by crystallizing a mixture having a composition in molar ratio listed in Table 4.

TABLE 4

| Reactants | Useful | Preferred |
|---|---|---|
| $YO_2/X_2O_3$ | 10 to infinity | 15-55 |
| $H_2O/YO_2$ | 1 to 10000 | 5-35 |
| $OH^-/YO_2$* | 0.001-0.39 | 0.1-0.35 |
| $OH^-/YO_2$** | 0.001-0.59 | 0.1-0.5 |
| $M/YO_2$ | 0.001-2 | 0.1-1 |
| $R/YO_2$ | 0.001-2 | 0.01-0.5 |
| Seed*** | 0-25 wt % | 1-5 wt % |
| R | HMI | HMI |

After crystallization, the MCM-22-P product has a composition in molar ratio listed in Table 5.

TABLE 5

| Reactants | Useful | Preferred |
|---|---|---|
| $YO_2/X_2O_3$ | 10 to infinity | 10-150 |
| $M/X_2O_3$ | 0.005-0.1 | |
| $R/X_2O_3$ | 1-4 | |
| R | HMI | |

(2) Acidic Composition

The acidic composition useful for this disclosure comprises an acidic solute and a solvent. The acidic solute comprises at least one of inorganic acid, such as, nitric acid hydrochloric acid and sulfuric acid, and organic acid, such as, oxalic acid and acetic acid, or any combination of inorganic acid and organic acid. Preferably, the acidic solute is nitric acid. The solvent comprises at least one of water, methanol, ethanol, acetone and dimethylsulfone (DMSO).

The acid concentration of the acidic composition is in the range of 0.001 to 10. The following acid concentrations are useful lower limits: 0.001, 0.01, 0.05, 0.1, 0.5, 1, 2, 3, 4, 5, 6, 7, 8, and 9. The following acid concentrations are useful upper limits: 0.01, 0.05, 0.1, 0.5, 1, 2, 3, 4, 5, 6, 7, 8, 9, and 10. The acid concentration falls in a range between any one of the above-mentioned lower limits and any one of the above-mentioned upper limits, so long as the lower limit is less than or equal to the upper limit. The acid concentration may be present in an amount ranging from 0.001 to 5 in one embodiment, alternatively 0.01 to 4, and alternatively 0.1 to 2.

The weight of acidic composition as used in the solid content over acidic composition weight ratios is calculated based on the total weight of acidic solute and solvent.

(3) Spacing Agent

Optionally, the acidic treatment step also comprises a spacing agent. The spacing agent useful is any agent capable of providing a moiety that can stabilize the precursor in expanded form (i.e. having the distinct (002) peak at 13.5±0.25 in both as-synthesized and calcined forms). For example, the spacing agent may be a silylating agent which is capable of providing a silicon moiety that can stabilize the precursor in expanded form.

Examples of compounds for spacing include organo-compounds of a tetravalent element, a trivalent element, and/or a pentavalent compounds, such as, organosilicon compound, organogermanium compound, orgnaotitanium compounds, organoboron compounds, organoaluminum compound, and organophorphous compound. The organosilicon silicon compounds may comprise a polysiloxane include silicones, a siloxane, and a silane including disilanes and alkoxysilanes.

Silicone compounds that can be used in the present invention include the following:

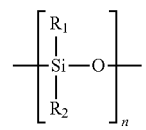

wherein $R_1$ is hydrogen, fluoride, hydroxy, alkyl, aralkyl, alkaryl or fluoro-alkyl. The hydrocarbon substituents generally contain from 1 to about 10 carbon atoms and preferably are methyl or ethyl groups. $R_2$ is selected from the same group as $R_1$, and n is an integer at least 2 and generally in the range of 2 to about 1000. The molecular weight of the silicone compound employed is generally between about 80 to about 20,000 and preferably about 150 to about 10,000. Representative silicone compounds include dimethylsilicone, diethylsilicone, phenylmethylsilicone, methyl hydrogensilicone, ethylhydrogensilicone, phenylhydrogensilicone, fluoropropylsilicone, ethyltrifluoroprophysilicone, tetrachlorophenyl methyl methylethylsilicone, phenylethylsilicone, diphenylsilicone, methyltrisilicone, tetrachlorophenylethyl-silicone, methylvinylsilicone and ethylvinylsilicone. The silicone compound need not be linear but may be cyclic as for example hexamethylcyclotrisiloxane, octamethylcyclotetrasiloxane, hexaphenyl cyclotrisiloxane and octaphenylcyclotetrasiloxane.

Mixtures of these compounds may also be used as well as silicones with other functional groups.

Useful siloxanes and polysiloxanes include as non-limiting example hexamethylcyclotrisiloxane, octamethylcyclotetrasiloxane, decamethylcyclopentasiloxane, hexamethyldisiloxane, octamethytrisiloxane, decamethyltetrasiloxane, hexaethylcyclotrisiloxane, octaethylcyclotetrasiloxane, hexaphenylcyclotrisiloxane and octaphenylcyclo-tetrasiloxane.

Useful silanes, disilanes, or alkoxysilanes include organic substituted silanes having the general formula:

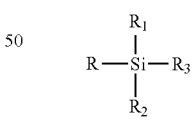

wherein R is a reactive group such as hydrogen, alkoxy, halogen, carboxy, amino, acetamide, trialkylsilyoxy, $R_1$, $R_2$ and $R_3$ can be the same as R or can be an organic radical which may include alkyl of from 1 to about 40 carbon atoms, alkyl or aryl carboxylic acid wherein the organic portion of alkyl contains 1 to about 30 carbon atoms and the aryl group contains about 6 to about 24 carbons which may be further substituted, alkylaryl and arylalkyl groups containing about 7 to about 30 carbon atoms. Preferably, the alkyl group for an alkyl silane is between about 1 and about 4 carbon atoms in chain length. Mixtures may also be used.

The silanes or disilanes include, as non-limiting examples, dimethylphenylsilane, phenytrimethylsilane, triethylsilane and hexamethyldislane. Useful alkoxysilanes are those with at least one silicon-hydrogen bond.

Molecular Sieve Preparation

A summary of the molecular sieves and/or zeolites, in terms of production, modification and characterization of molecular sieves, is described in the book "Molecular Sieves—Principles of Synthesis and Identification"; (R. Szostak, Blackie Academic & Professional, London, 1998, Second Edition). In addition to molecular sieves, amorphous materials, chiefly silica, aluminum silicate and aluminum oxide, have been used as adsorbents and catalyst supports. A number of long-known forming techniques, like spray drying, pilling, pelletizing and extrusion, have been and are being used to produce macrostructures in the form of, for example, spherical particles, extrudates, pellets and tablets of both micropores and other types of porous materials for use in catalysis, adsorption and ion exchange. A summary of these techniques is described in "Catalyst Manufacture," A. B. Stiles and T. A. Koch, Marcel Dekker, New York, 1995.

To the extent desired, the original metal cations of the as-synthesized material can be replaced in accordance with techniques well known in the art, at least in part, by ion exchange with other cations. Preferred replacing cations include metal ions, hydrogen ions, hydrogen precursor, e.g., ammonium, ions and mixtures thereof Particularly preferred cations are those which tailor the catalytic activity for certain hydrocarbon conversion reactions.

These include hydrogen, rare earth metals and metals of Groups 1-17, preferably Groups 2-12 of the Periodic Table of the Elements.

The EMM-13 crystalline molecular sieve of this disclosure should be generally dehydrated, at least partially. This can be done by heating to a temperature in the range of e.g., 200° C. to 595° C. in an atmosphere such as air or nitrogen, and at atmospheric, sub-atmospheric or super-atmospheric pressures for e.g., between 30 minutes and 48 hours. The degree of dehydration is measured by the percentage of weight loss relative to the total weight loss of a molecular sieve sample at 595° C. under flowing dry nitrogen (less than 0.001 kPa partial pressure of water vapor) for 48 hours. Dehydration can also be performed at room temperature (~25° C.) merely by placing the silicate in a vacuum, but a longer time is required to obtain a sufficient amount of dehydration.

The EMM-13 crystalline molecular sieve of this disclosure especially in its metal, hydrogen and ammonium forms can be beneficially converted to another form by thermal treatment. This thermal treatment is generally performed by heating one of these forms at a temperature at least 370° C. for at least one minute and generally not longer than 1000 hours. While sub-atmospheric pressure can be employed for the thermal treatment, atmospheric pressure is desired for reasons of convenience. The thermal treatment can be performed at a temperature up to about 925° C. The thermal treated product is particularly useful in the catalysis of certain hydrocarbon conversion reactions. The thermally treated product, especially in its metal, hydrogen and ammonium forms, is particularly useful in the catalysis of certain organic, e.g., hydrocarbon, conversion reactions. Non-limiting examples of such reactions include those described in U.S. Pat. Nos. 4,954,325; 4,973,784; 4,992,611; 4,956,514; 4,962,250; 4,982,033; 4,962,257; 4,962,256; 4,992,606; 4,954,663; 4,992,615; 4,983,276; 4,982,040; 4,962,239; 4,968,402; 5,000,839; 5,001,296; 4,986,894; 5,001,295; 5,001,283; 5,012,033; 5,019,670; 5,019,665; 5,019,664; and 5,013,422, each incorporated herein by reference as to the description of the catalytic reactions.

The EMM-13 crystalline molecular sieve of this disclosure can be shaped into a wide variety of particle sizes. Generally speaking, the particles can be in the form of a powder, a granule, or a molded product, such as an extrudate. In cases where the catalyst is molded, such as by extrusion, the crystals can be extruded before drying or partially dried and then extruded.

It is desired to incorporate the EMM-13 molecular sieve with another material resistant to the temperatures and other conditions employed in alkylation processes. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the EMM-13 molecular sieve, i.e. combined therewith or present during synthesis of the EMM-13, which is active, tends to change the conversion and/or selectivity of the catalyst. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. The materials, i.e. clays, oxides, etc., function as binders for the catalyst. It is desirable to provide a catalyst having good crush strength because in commercial use it is desirable to prevent the catalyst from breaking down into powder-like materials. These clay binders have been employed normally only for the purpose of improving the crush strength of the catalyst.

Naturally occurring clays which can be composited with the EMM-13 molecular sieve include the montmorillonite and kaolin family, which families include the subbentonites, and the kaolins commonly known as Dixie, McNamee, Georgia and Florida clays or others in which the main mineral constituent is halloysite, kaolinite, dictite, narcite, or anauxite. Such clays can be used in the raw state as originally mined or initially subjected to calcination, treatment or chemical modification. Binders useful for compositing with the present crystal also include inorganic oxides, notably alumina In addition to the foregoing materials, the EMM-13 molecular sieve can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of finely divided EMM-13 crystalline molecular sieve and inorganic oxide matrix vary widely, with the crystal content ranging from about 1 to about 99 percent by weight and more usually, particularly when the composite is prepared in the form of beads, in the range of about 20 to about 80 wt % of the composite.

The following examples reflect embodiments of the invention and are by no means intended to be limiting of the scope of the invention.

Experiments

Powder X-ray Diffraction

Powder x-ray data were obtained on a Bruker D4 instrument in Bragg-Brentano geometry with monochromatic Cu Kα radiation; the pattern used for structural characterization extended from 1.2 to 80° in 2θ. Intensities for Rietveld refinement were extracted from the continuous scans. Indexing of powder patterns were carried out with the tool in the MDI Inc. program JADE.

Indexing of powder patterns were carried out with the tool in the MDI Inc. program JADE. After construction of a trial model (facilitated by the structure building module in Cerius$^2$ (Accelrys, Inc.)), its fit to the powder diffraction profile was made via Rietveld refinements with the program GSAS as described in A. C. Larsson & R. B. von Dreele, *General Structure Analysis System, GSAS*, Los Alamos National Laboratory, Los Alamos, New Mex., 1994. Sometimes the framework would be optimized geometrically with the program DLS as described in Ch. Baerlocher, A. Hepp, & W. M. Meier, *Distance Least Squares Refinement Program, DLS*-76. ETH, Zürich, 1977. Electron density maps generated with GSAS could be used to locate additional atoms in the unit cell, tested first with Cerius$^2$ models to ensure that there would be no collision with framework atoms. Care was taken during refinements to avoid unusual bonding geometries. For the framework, this was partially ensured by imposing a restraint to the Si—O bond distances (1.61±0.03 Å) and O—O tetrahedral distances (2.65±0.06 Å). A weighting function for the framework refinement was gradually relaxed but, after each refinement step, the chemical reasonableness of the bonding geometry was ascertained. In addition to unit cell parameters, background and zero shift, profile functions were also refined to improve the model fit but it was sometimes seen that the usual R-values did not necessarily denote a close match of the model to the experimental intensity curve. In several cases, adjustments were made for preferred orientation, expected for Bragg-Brentano data from a platy crystal assembly according to R. A. Young, in: *The Rietveld Method* (R. A. Young, ed.). Oxford Univ. Press, Oxford, 1995, p. 11.

Surface Areas

The overall surface area of a molecular sieve may be measured by the Brunauer-Emmett-Teller (BET) method using adsorption-desorption of nitrogen (temperature of liquid nitrogen, 77 K). The internal surface area (ZSA, m$^2$/g) may be calculated using t-plot of the Brunauer-Emmett-Teller (BET) measurement. The external surface area (ZSA, m$^2$/g) is calculated by subtracting the internal surface area from the overall surface area measured by the Brunauer-Emmett-Teller (BET) measurement. Micro-pore volume (M-pore in cm$^3$/g) is determined by nitrogen adsorption/desorption (nitrogen isotherm).

Collidine Number Measurement

The collidine number of a molecular sieve may be measured by TGA, A sample is dried at 200° C. to constant weight (weight change less than ±1% for the period of 1 hour). The weight of the dried sample, the sorbate, is then measured. The sorbent, 2,4,6-collidine, is delivered by a sparger maintained at 3 Torr collidine partial pressure and carried over the sample by nitrogen passed 200 ml/min for 60 min. The collidine number is expressed as micromoles of adsorbed per gram of the sorbate.

Electron Microscopy and Diffraction

Selected area electron diffraction experiments were carried out at 300 kV with an FEI/Philips CM-30 electron microscope using a selected area diameter of 0.25 µm. In some cases, three-dimensional tilts were made around a defined reciprocal lattice to map out a 3-D reciprocal lattice. Bright field electron micrographs were obtained at 32,240× direct magnification. The field-limiting aperture passed diffraction information out to d*=0.08 Å$^{-1}$. All exposures were recorded on Kodak Biomax MS film.

For preliminary intensity data collection, diffraction films were digitized on a flat bed scanner and, after their indexing, the intensities of individual spots were estimated with the program ELD according to X. D. Zou, Yu. Sukharev & S. Hovmöller, Ultramicroscopy 53 (1994) 271 within the CRISP as described in S. Hovmöller, Ultramicroscopy 41 (1992) 121 package. Symmetry-related reflections were averaged and no Lorentz correction was applied to the derived structure factor magnitudes. In some cases it was difficult to obtain suitable peak integration with ELD. In this case, films were scanned on a flat bed Joyce Loebl Mk. III microdensitometer and the peak areas used as an estimate of their intensities. For merging data into a three-dimensional set, common reflections from separate zones were used for scaling one set to the other as discussed in D. L. Dorset, *Structural Electron Crystallography*. Plenum, NY, 1995.

For electron diffraction studies, structure factor calculations were carried out with the Fortran program SF and one-dimensional electrostatic potential distributions were obtained with the Fortran program ZPOT after phase approximates from a known structure were provided.

Three-dimensional tilts around defined unit cell reciprocal axes (generally a*) were plotted to give an undistorted view of the three-dimensional reciprocal lattice. Using the usual gold powder standard for calibration, the dimensions of the complete unit cell could be measured. From systematic absences in these plots, the unit cell symmetry could also be estimated according to Th. Hahn (ed.), *International Tables for Crystallography. Volume A. Space-Group Symmetry*. Kluwer, Dordrecht, 1995.

Structures were found from a 3-D dataset using maximum entropy and likelihood with the program MICE according to C. J. Gilmore, K. Shankland, & G. Bricogne, Proc. Roy. Soc. London 442 (1993) 97. It is useful to utilize a typical zeolite density histogram as described in Ch. Baerlocher, L. B. McCusker & L. Palatinus, Z. Krist. 222 (2007) 47 to further discriminate among trial structural solutions culled by a maximum likelihood figure of merit according to C. J. Gilmore, G. Bricogne & C. Bannister, Acta Cryst. A46 (1990) 297. Instead of full factorial phase permutation of identified reflections, a Nordström-Robinson error correcting code according to C. J. Gilmore, W. Dong, & G. Bricogne, Acta Cryst. A55 (1999) 70 was used to speed up the calculation.

Materials and Synthesis

EXAMPLE 1

Synthesis of MCM-22-P with Si/Al2~60

The synthesis mixture was prepared with 184 g of water, 1.5 g of Usalco 45, 22 g of 10% NaOH, 17 g of hexamethyleneimine and 23 g of Ultrasil. It was reacted at 150° C. with 100 RPM in a 300 ml autoclave. Product composition and structural porosity characteristics are listed in Table 6.

EXAMPLE 2

Synthesis of MCM-22-P with Si/Al2~23

The synthesis was analogous to Example 1, U.S. Pat. No. 4,954,325. Product composition and structural porosity characteristics are listed in Table 6.

EXAMPLE 3a

Acid Treatment of MCM-22-P (Example 1) with Silane to Produce EMM-13 As-Synthesized and EMM-13 Calcined Mixing 30 grams of 1 M HNO$_3$ solution (obtained by mixing 3 g of concentrated acid with 27 g of water) with 0.3 g of spacing agent (silylating agent) dimethyldiethoxy silane, and followed with adding 3 g of as-synthesized MCM-22-P sample of Example 1. The mixture was reacted at 170° C. for 24 hrs. The product was filtered, washed with water and dried. The as-treated material was identified by XRD as EMM-13 as-synthesized. The as-treated material was further calcined in air at 540° C. for 4 hrs. The calcined material of example 3a was identified by XRD as EMM-13 calcined. Product composition and structural porosity characteristics are listed in Table 6.

EXAMPLE 3b

Acid Treatment of MCM-22-P (Example 1) to Produce EMM-13 As-Synthesized and EMM-13 Calcined Mixing 30 grams of 1 M $HNO_3$ solution (obtained by mixing 3 g of concentrated acid with 27 g of water), and followed with adding 3 g of as-synthesized MCM-22-P sample of Example 1. The mixture was reacted at 170° C. for 24 hrs. The product was filtered, washed with water and dried. The as-treated material was identified by XRD as EMM-13 as-synthesized. The as-treated material was further calcined in air at 540° C. for 4 hrs. The calcined material of example 3b was identified by XRD as EMM-13 calcined. Product composition and structural porosity characteristics are listed in Table 6.

EXAMPLE 3c

Acid Treatment of MCM-22-P (Example 1) with Silica to Produce EMM-13 As-Synthesized and EMM-13 Calcined Mixing 30 grams of 1 M $HNO_3$ solution (obtained by mixing 3 g of concentrated acid with 27 g of water) with 0.3 g of fumed silica (Cab-o-Sil), and followed with adding 3 g of as-synthesized MCM-22-P sample of Example 1. The mixture was reacted at 170° C. for 24 hrs. The product was filtered, washed with water and dried. The as-treated material was identified by XRD as EMM-13 as-synthesized. The as-treated material was further calcined in air at 540° C. for 4 hrs. The calcined material of example 3c was identified by XRD as EMM-13 calcined. Product composition and structural porosity characteristics are listed in Table 6.

EXAMPLE 4a

Acid Treatment of MCM-22-P (Example 2) with Silane to Produce MCM-22-P and MCM-22

Mixing 30 grams of 1 M $HNO_3$ solution (obtained by mixing 3 g of concentrated acid with 27 g of water) with 0.3 g of spacing agent (silylating agent) dimethyldiethoxy silane, and followed with adding 3 g of as-synthesized MCM-22-P sample of Example 2. The mixture was reacted at 170° C. for 24 hrs. The product was filtered, washed with water and dried. The as-treated material was identified by XRD as MCM-22-P. The as-treated material was further calcined in air at 540° C. for 4 hrs. The calcined material of example 4a was identified by XRD as MCM-22. Product composition and structural porosity characteristics are listed in Table 6.

EXAMPLE 4b

Acid Treatment of MCM-22-P (Example 1) to Produce MCM-22

Mixing 30 grams of 1 M $HNO_3$ solution (obtained by mixing 3 g of concentrated acid with 27 g of water), and followed with adding 3 g of as-synthesized MCM-22-P sample of Example 2. The mixture was reacted at 170° C. for 24 hrs. The product was filtered, washed with water and dried. The as-treated material was identified by XRD as MCM-22-P. The as-treated material was further calcined in air at 540° C. for 4 hrs. The calcined material of example 4b was identified by XRD as MCM-22. Product composition and structural porosity characteristics are listed in Table 6.

TABLE 6

| | \multicolumn{7}{c}{Example} |
|---|---|---|---|---|---|---|---|
| | 1 | 3a | 3b | 3c | 2 | 4a | 4b |
| \multicolumn{8}{c}{Synthesis conditions} |
| $Si/Al_2$ | 87 | | | | 29.9 | | |
| Si + Al | 8.7 | | | | 13.9 | | |
| OH/Si | 0.18 | | | | 0.17 | | |
| R/Si | 0.49 | | | | 0.35 | | |
| T (C.) | 150 | | | | 150 | | |
| Time (hr) | 76 | | | | 60-70 | | |
| \multicolumn{8}{c}{Acid treatment conditions} |
| T (° C.) | | 170 | 170 | 170 | | 170 | 170 |
| Time (hr) | | 24 | 24 | 24 | | 24 | 24 |
| \multicolumn{8}{c}{Product Characterization and Properties} |
| XRD | MCM-22-P + trace ZSM-12 | EMM-13 as-synthesized | EMM-13 as-synthesized | EMM-13 as-synthesized | MCM-22-P | MCM-22-P | MCM-22-P |
| $Al_2O_3$ | 2.3 | 2.16 | 2.1 | | | | 4.88 |
| Na | 0.4 | 0.0339 | 0.267 | | | | 0.0789 |
| $SiO_2$ | 78.9 | 85.3 | 78.7 | | | | 76 |
| $Si/Al_2$ | 58.32 | 67.13 | 63.71 | | | | 26.48 |
| \multicolumn{8}{c}{Product Characterization and Properties after Calcination in Air at 540° C. for 4 hrs} |
| XRD | MCM-22 | EMM-13 | EMM-13 | EMM-13 | MCM-22 | MCM-22 | MCM-22 |
| BET | 410 | 485 | 463 | 396 | | 436 | 472 |
| ZSA | 378 | 456 | 404 | 327 | | 329 | 362 |

TABLE 6-continued

| | Example | | | | | | |
|---|---|---|---|---|---|---|---|
| | 1 | 3a | 3b | 3c | 2 | 4a | 4b |
| MSA | 32 | 29 | 58 | 68 | | 107 | 110 |
| M-pore | 0.152 | 0.18 | 0.16 | 0.13 | | 0.13 | 0.15 |
| Collidine | | 214 | 153 | | 124 | | |

EXAMPLE 5

Synthesis of 40/1 MCM-22-P

The preparation was carried out like above but with a gel having the following molar ratio of reactants: silica/alumina=54/1, OH/Si=0.15, water/Si=35, R/Si=0.58. The mixture was heated at 170° C. for 70 hrs and product isolated by standard methods.

EXAMPLES 6-17

Synthesis EMM-13 with 40/1 MCM-22-P

Examples 6-17 were conducted by mixing concentrated acid with water to form acid solution according to Table 7. Various amount of spacing agent (silylating agent) dimethyldiethoxy silane, were added followed by as-synthesized MCM-22-P sample of Example 5 according to Table 7. The mixtures were reacted at treatment conditions including a treatment temperature and time according to Table 7. The products were filtered, washed with water and dried. Calcination of the products was carried out in air at 540° C. for 4 hrs. The as-treated materials were further calcined in air at 540° C. for 4 hrs. The calcined materials of Example 6-11 and 13-17 were identified by XRD as EMM-13.

taining MCM-22 catalyst. All feed pretreatment materials were dried in a 260° C. oven for 12 hours before using.

Nitrogen

Nitrogen was ultra high purity grade and obtained from a commercial specialty gases source.

EXAMPLE 18

Preparation of the Metal Containing Inorganic Oxide

A commercially available gamma-alumina (Catalox™ HTA-101) was slurried in water with a commercially available palladium salt (target 0.6 wt. % Pd), dried overnight at 121° C. followed by calcination at 538° C. in air to convert the palladium salt to palladium oxide. The palladium containing alumina was milled to less than 10 microns.

EXAMPLE 19

Benzene Hydroalkylation

A EMM-13 composite sample of Examples 7, 8, 11, 12, 13, 15, and 17 was exchanged with 1 N ammonium nitrate and calcined at 540° C. to convert to the H-form of EMM-13. A catalyst containing 41 wt % H-form of EMM-13 and 59 wt % palladium-containing alumina catalyst of Example18 was

TABLE 7

| | Amount, grams | | | | | | Surface Area, m2/g | | | Collidine |
|---|---|---|---|---|---|---|---|---|---|---|
| | | 40/1 Si/Al2 | | | | | | | | |
| Example | Water | Conc HNO3 | MCM-22-P | Silane | Time, hours | Temp, ° C. | Total BET | Zeolite ZSA | Mesopore, MSA | umole/g |
| Parent | 40/1 Si/Al2 | MCM-22-P | | | | | 521 | 478 | 43 | 44 |
| 6 | 9.5 | 0.5 | 0.4 | 0.02 | 24 | 170 | 568 | 485 | 83 | 350 |
| 7 | 7.25 | 2.75 | 1.7 | 0.21 | 17 | 145 | 600 | 540 | 60 | 244 |
| 8 | 9.5 | 0.5 | 3 | 0.02 | 10 | 170 | 615 | 544 | 71 | 262 |
| 9 | 5 | 5 | 0.4 | 0.02 | 10 | 120 | 642 | 573 | 69 | 195 |
| 10 | 5 | 5 | 0.4 | 0.4 | 10 | 170 | 492 | 462 | 30 | 134 |
| 11 | 9.5 | 0.5 | 3 | 0.4 | 10 | 120 | 623 | 565 | 58 | 327 |
| 12 | 5 | 5 | 3 | 0.02 | 24 | 120 | 556 | 480 | 76 | 89 |
| 13 | 9.5 | 0.5 | 0.4 | 0.4 | 24 | 120 | 533 | 499 | 34 | 266 |
| 14 | 5 | 5 | 3 | 0.4 | 24 | 170 | 675 | 609 | 66 | 311 |
| 15 | 7.25 | 2.75 | 1.7 | 0.21 | 17 | 145 | 609 | 547 | 62 | 245 |
| 16 | 8.62 | 1.38 | 3 | 0.5 | 17 | 90 | 642 | 588 | 55 | 212 |
| 17 | 135 | 15 | 15 | 2 | 10 | 120 | 803 | 735 | 69 | 351 |

Feed Pretreatment

Benzene

Benzene was obtained from a commercial source. The benzene was passed through a pretreatment vessel containing equal parts (by volume) molecular sieve 13X, molecular sieve 4A, Engelhard F-24 Clay, and Selexsorb CD (in order from inlet to outlet), and then through a pretreatment vessel conformulated. This catalyst was tested for benzene hydroalkylation to form cyclohexylbenzene.

Feed Pretreatment

The experiment was conducted in a fixed bed ⅜" OD tubular reactor in a downflow configuration with an ⅛" internal thermocouple. The reactor furnace was controlled in isothermal mode. Two grams of catalyst sized to 14/25 mesh was loaded into the ⅜" reactor. Experiment was conducted with catalyst as 14/25 mesh loaded into the ⅜" reactor. The catalyst bed was axially centered in the middle furnace zone. The catalyst was packed with inert sand to fill the interstitial void spaces. Reaction conditions were 156° C., 1076 kPa-g and the hydrogen to benzene molar ratio was 0.69. Weight hourly space velocity was 1.05 hr$^{-1}$ on a benzene basis.

The benzene conversion was approximately 34 wt %, and the cyclohexylbenzene to di-cyclohexylbenzene (weight) ratio was approximately 28.

We claim:

1. A process for the hydroalkylation of an aromatic compound comprising the step of contacting the aromatic compound with hydrogen in the presence of a catalyst system comprising a first hydrogenation metal having hydrogenation activity and a molecular sieve having alkylation activity to produce a cycloalkyl-substituted aromatic compound, wherein said molecular sieve comprises a framework of tetrahedral atoms bridged by oxygen atoms, the tetrahedral atom framework being defined by a unit cell with atomic coordinates in nanometers shown in the following table:

| Atom | x/a | y/b | z/c | Uiso | occ. |
|---|---|---|---|---|---|
| T1 | 0.6667 | 0.3333 | 0.1126(2) | 0.00649 | 1.0 |
| T2 | 0.4652(5) | 0.2326(3) | 0.1754(3) | | |
| T3 | 0.3901(5) | 0.0 | 0.1897(4) | | |
| T4 | 0.6667 | 0.3333 | 0.2403(4) | | |
| T5 | 0.6667 | 0.3333 | 0.3575(4) | | |
| T6 | 0.3894(5) | 0.0 | 0.3050(4) | | |
| T7 | 0.4215(5) | 0.2108(2) | 0.3593(3) | | |
| T8 | 0.2502(5) | 0.1251(3) | 0.4450(2) | | |
| T9 | 0.6667 | 0.3333 | 0.0 | | |
| O10 | 0.6667 | 0.3333 | 0.0562(1) | 0.010 | 1.0 |
| O11 | 0.5420(3) | 0.2710(1) | 0.1282(2) | | |
| O12 | 0.3876(5) | 0.1037(2) | 0.1681(4) | | |
| O13 | 0.5408(3) | 0.2704(2) | 0.2230(3) | | |
| O14 | 0.6667 | 0.3333 | 0.2991(4) | | |
| O15 | 0.3725(2) | 0.0 | 0.2473(3) | | |
| O16 | 0.5 | 0.0 | 0.176(1) | | |
| O17 | 0.5 | 0.0 | 0.318(1) | | |
| O18 | 0.3951(6) | 0.1062(3) | 0.3279(3) | | |
| O19 | 0.5453(3) | 0.2727(1) | 0.3786(4) | | |
| O20 | 0.3519(7) | 0.1759(4) | 0.4087(3) | | |
| O21 | 0.1806(5) | 0.0 | 0.4320(3) | | |
| O22 | 0.2928(8) | 0.1464(4) | 0.5 | | |
| Extra-framework: | | | | | |
| T23 | 0.4499 | 0.1812 | 0.0686 | 0.025 | 0.355 |
| T24 | 0.2477 | 0.1232 | 0.0360 | 0.025 | 0.160 |
| Approximate | | | | | |
| O25 | 0.663 | 0.452 | 0.0 | 0.025 | 0.099 |

2. The process of claim 1, wherein said molecular sieve further has a composition involving the molar relationship:

$X_2O_3$:(n)$YO_2$, wherein X is a trivalent element comprises at least one of aluminum, boron, iron and gallium, Y is a tetravalent element comprises at least one of silicon and germanium, and n is at least about 30.

3. The process of claim 1, wherein said molecular sieve further has, in the as-synthesized form, having a formula, on an anhydrous basis and in terms of moles of oxides per n moles of $YO_2$, as follows:

(0.005-1)$M_2O$:(1-4)R:$X_2O_3$:n$YO_2$ wherein M is an alkali or alkaline earth metal, n is at least about 30 and R is an organic moiety.

4. The process of claim 2, wherein said n is from about 30 to about 150.

5. The process of claim 2, wherein X is aluminum and Y is silicon.

6. The process of claim 1, wherein the molecular sieve comprises less than 1 wt % Ti.

7. The process of claim 1, wherein the molecular sieve has a collidine adsorption capacity at least 150 moles/g.

8. The process of claim 1, wherein said molecular sieve further has, in its as-synthesized form and in calcined form, an X-ray diffraction pattern including peaks at d-spacing maxima at 13.18±0.25, 12.33±0.23, 11.05±0.2 and 9.31±0.2 Angstroms, wherein said peaks at d-spacing maxima at 11.05±0.2 and 9.31±0.2 Angstroms exhibit a valley in between and the measured intensity corrected for background at the lowest point of said valley is less than 50% of the intensity point at the same XRD d-spacing on the line connecting d-spacing maxima at 11.05±0.2 and 9.31±0.2 Angstroms.

9. The process of claim 8, wherein said molecular sieve further has, in its as-synthesized form and in calcined form, an X-ray diffraction pattern including peaks at 6.9±0.15, 3.57±0.07 and 3.42±0.07 Angstroms.

10. The process of claim 1, wherein said aromatic compound is selected from the group consisting of benzene, naphthalene, anthracene, naphthacene, perylene, coronene, phenanthrene, xylene, n-propylbenzene, alpha-methylnaphthalene, o-diethylbenzene, m-diethylbenzene, p-diethylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; 3-methyl-phenanthrene and mixtures thereof.

11. The process of claim 1, wherein said aromatic compound is benzene.

12. The process of claim 1, the process conducted under hydroalkylation reaction conditions including a temperature of from about 100° C. to about 400° C., a pressure of from about 500 to about 5000 kPa, a molar ratio of aromatic compound to hydrogen from about 0.01 to about 100, and a feed weight hourly space velocity (WHSV) based on the alkylating agent of from about 0.1 to 500 hr$^{-1}$.

13. The process of claim 1, wherein said aromatic compound comprises benzene, and said hydroalkylation reaction conditions include a temperature of from about 50° C. to about 350° C., a pressure of from about 100 to about 7000 kPa-a, a molar ratio of aromatic compound to hydrogen of from about 0.01 to about 100, and a feed weight hourly space velocity (WHSV) of from about 0.01 to 100 hr$^{-1}$.

14. The process of claim 1, wherein said aromatic compound comprises benzene and said hydroalkylation reaction conditions include a temperature of from about 10° C. to about 250° C., a pressure of from about 100 to about 3000 kPa-a, a molar ratio of hydrogen to benzene of from about 0.0.4 to about 0.9 and a feed weight hourly space velocity (WHSV) based on benzene of from about 0.01 to 250 hr$^{-1}$.

15. The process of claim 1, wherein a monocycloalkyl-substituted aromatic compound and a dicycloalkyl-substituted compound are produced at a ratio of monocycloalkyl-substituted aromatic compound to dicycloalkyl-substituted compound of greater than about 10.

16. The process of claim 1, wherein said aromatic compound comprises benzene and wherein cyclohexylbenzene and dicyclohexylbenzene are produced at a ratio of cyclohexylbenzene to dicyclohexylbenzene of greater than about 10.

17. The process of claim 1, wherein at least a portion of the hydrogenation metal is supported on an inorganic oxide different from the molecular sieve.

18. The process of claim 17, wherein the hydrogenation metal is applied to the inorganic oxide before the inorganic oxide is composited with the molecular sieve.

19. The process of claim 1, wherein the first hydrogenation metal is selected from palladium, ruthenium, nickel and cobalt.

20. The process of claim 1 wherein the catalyst system also contains a second hydrogenation metal, different from the first hydrogenation metal, and selected from zinc, tin, nickel and cobalt.

21. The process of claim 1, wherein the contacting step produces a mono-cycloalkyl-substituted aromatic compound and a di-cycloalkyl-substituted aromatic compound, and further comprising a transalkylating step comprising contacting the di-cycloalkyl-substituted aromatic compound with additional aromatic compound in the presence of a transalkylation catalyst to produce additional mono-cycloalkyl-substituted aromatic compound.

22. The process of claim 21, wherein the hydroalkylation and transalkylation steps are effected in separate reactors.

23. The process of claim 21, wherein the transalkylation catalyst comprises a molecular sieve and the transalkylation step comprises at least partial liquid phase conditions comprising a temperature of abuot 100° C. to about 300° C., a pressure of about 800 to 3500 kPa, a weight hourly space velocity of about 1 to about 10 hr−1 on total feed, a mono-cycloalkyl-substituted aromatic compound/di-cycloalkyl-substituted aromatic compound weight ratio of about 1:1 to about 5:1, or a combination thereof.

* * * * *